(12) United States Patent
Han et al.

(10) Patent No.: US 10,131,680 B1
(45) Date of Patent: Nov. 20, 2018

(54) GROUP 4 METAL ELEMENT-CONTAINING ALKOXY COMPOUND, PREPARING METHOD THEREOF, PRECURSOR COMPOSITION INCLUDING THE SAME FOR FILM DEPOSITION, AND METHOD OF DEPOSITING FILM USING THE SAME

(71) Applicant: UP CHEMICAL CO., LTD., Pyeongtaek-si, Gyeonggi-do (KR)

(72) Inventors: Won Seok Han, Pyeongtaek-si (KR); Wonyong Koh, Daejeon (KR); Myeong-Ho Park, Suwon-si (KR)

(73) Assignee: UP CHEMICAL CO., LTD., Pyeongtaek-si, Gyeonggi-do (KR)

( * ) Notice: Subject to any disclaimer, the term of this patent is extended or adjusted under 35 U.S.C. 154(b) by 0 days.

(21) Appl. No.: 15/578,028

(22) PCT Filed: Aug. 8, 2017

(86) PCT No.: PCT/KR2017/008528
§ 371 (c)(1),
(2) Date: Nov. 29, 2017

(30) Foreign Application Priority Data

Jun. 14, 2017 (KR) .......... 10-2017-0074938
Aug. 2, 2017 (KR) .......... 10-2017-0098165
Aug. 3, 2017 (KR) .......... 10-2017-0098413

(51) Int. Cl.
| | | |
|---|---|---|
| C07F 7/28 | (2006.01) | |
| C01G 27/02 | (2006.01) | |
| C23C 16/40 | (2006.01) | |
| C07F 7/00 | (2006.01) | |
| C23C 16/455 | (2006.01) | |
| C01G 25/02 | (2006.01) | |
| C01G 23/04 | (2006.01) | |
| C09D 1/00 | (2006.01) | |

(52) U.S. Cl.
CPC .......... *C07F 7/28* (2013.01); *C01G 23/04* (2013.01); *C01G 25/02* (2013.01); *C01G 27/02* (2013.01); *C07F 7/00* (2013.01); *C09D 1/00* (2013.01); *C23C 16/405* (2013.01); *C23C 16/45553* (2013.01)

(58) Field of Classification Search
CPC .......... C23C 16/405; C07F 7/28
See application file for complete search history.

(56) References Cited

U.S. PATENT DOCUMENTS

| 10,005,795 B1* | 6/2018 | Han .......... C07F 7/00 |
| 2004/0220359 A1 | 11/2004 | Abhari et al. |
| 2011/0020547 A1* | 1/2011 | Gatineau .......... C07F 17/00 427/255.28 |

FOREIGN PATENT DOCUMENTS

| KR | 1020060014892 A | 2/2006 |
| KR | 1020060086193 A | 7/2006 |
| KR | 1020070121281 A | 12/2007 |
| KR | 1020130118713 A | 10/2013 |
| KR | 1020150143371 A | 12/2015 |

OTHER PUBLICATIONS

Christie et al (Novel Routes to Bidentate Cyclopentadienyl-Alkoxide Complexes of Titanium: Synthesis of (η5-σ-C5R14CHR2CH2CR3R4O)TiCl2), Organometallics, (1999), 18, pp. 348-359) (Year: 1999).*
Sara N. Paisner et al., "Formation of planar-chiral alkylphosphine- and aniline-substituted cyclopentadienyl metal complexes and their reactivity toward electrophiles", Inorganica Chimica Acta vol. 334 (Jan. 2002), pp. 253-275.
Jiri Pinkas et al., "Transformations of functional groups attached to cyclopentadienyl or related ligands in group 4 metal complexes", Coordination Chemistry Reviews vol. 296 (Jul. 2015), pp. 45-90.

* cited by examiner

*Primary Examiner* — Melvin C. Mayes
*Assistant Examiner* — Michael Forrest
(74) *Attorney, Agent, or Firm* — Brundidge & Stanger, P.C.

(57) ABSTRACT

The present disclosure provides a Group 4 metal element-containing novel alkoxy compound, a method of preparing the Group 4 metal element-containing alkoxy compound, a precursor composition including the Group 4 metal element-containing alkoxy compound for depositing a film, and a method of depositing a Group 4 metal element-containing film using the precursor composition.

7 Claims, 5 Drawing Sheets

GROUP 4 METAL ELEMENT-CONTAINING ALKOXY COMPOUND, PREPARING METHOD THEREOF, PRECURSOR COMPOSITION INCLUDING THE SAME FOR FILM DEPOSITION, AND METHOD OF DEPOSITING FILM USING THE SAME

CROSS-REFERENCE TO RELATED APPLICATIONS

This Application is the National Stage filing under 35 U.S.C. § 371 of PCT Application Ser. No. PCT/KR2017/008528 filed on Aug. 8, 2017, which claims the benefit under 35 U.S.C. § 119(a) of Korean Patent Application No. 10-2017-0074938 filed on Jun. 14, 2017, Korean Patent Application No. 10-2017-0098165 filed on Aug. 2, 2017, and Korean Patent Application No. 10-2017-0098413 filed on Aug. 3, 2017, the entire disclosures of which are incorporated herein by reference.

TECHNICAL FIELD

The present disclosure relates to a Group 4 metal element-containing alkoxy novel compound, a method of preparing the Group 4 metal element-containing alkoxy compound, a precursor composition including the Group 4 metal element-containing alkoxy compound for depositing a film, and a method of depositing a Group 4 metal element-containing film using the precursor composition.

BACKGROUND

A compound containing a Group 4 metal element such as Ti, Zr, and Hf is used as a catalyst for polymer synthesis, or used for preparing an oxide or nitride film containing a Group 4 metal element, e.g., a zirconium oxide film, a titanium nitride film, etc., which is used as a high-k material, an electrode, etc. to manufacture a semiconductor device. However, when a film containing a Group 4 metal element is formed by chemical vapor deposition (CVD) or atomic layer deposition (ALD), there is still a need for developing of a Group 4 metal element-containing novel compound for forming a uniform film containing a Group 4 metal element, and particularly, there is still a need for developing a Group 4 metal element-containing novel compound which can be usefully utilized as a precursor for forming a Group 4 metal element-containing uniform film or thin film on the entire surface of a substrate having a fine trench (groove) or porous substrate, including a surface of the trench (groove) and a surface of the substrate.

Meanwhile, Korean Patent Laid-open Publication No. 2007-0121281 discloses "a precursor for zirconium dioxide thin film deposition and a preparation method thereof".

DISCLOSURE OF THE INVENTION

Problems to be Solved by the Invention

The present disclosure is conceived to provide a Group 4 metal element-containing novel alkoxy compound, a method of preparing the Group 4 metal element-containing alkoxy compound, a precursor composition including the Group 4 metal element-containing alkoxy compound for depositing a film, and a method of depositing a Group 4 metal element-containing film using the precursor composition.

However, problems to be solved by the present disclosure are not limited to the above-described problems. Although not described herein, other problems to be solved by the present disclosure can be clearly understood by those skilled in the art from the following description.

Means for Solving the Problems

According to a first aspect of the present disclosure, there is provided a Group 4 metal element-containing compound, represented by the following Chemical Formula 1:

[Chemical Formula 1]

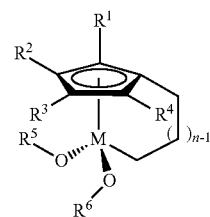

in the above Chemical Formula 1, M is Ti, Zr or Hf, each of $R^1$ to $R^4$ is independently hydrogen or a linear or branched alkyl group having 1 to 4 carbon atoms, each of $R^5$ and $R^6$ is independently a linear or branched alkyl group having 1 to 4 carbon atoms, and n is an integer of from 1 to 3.

According to a second aspect of the present disclosure, there is provided a method of preparing a Group 4 metal element-containing compound, represented by the following Chemical Formula 1, including reacting a compound represented by the following Chemical Formula 2 with a linear or branched alcohol as $R^5OH$ and/or $R^6OH$ having 1 to 4 carbon atoms:

[Chemical Formula 2]

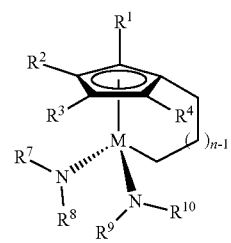

in the above Chemical Formula, M is Ti, Zr or Hf, each of $R^1$ to $R^4$ is independently hydrogen or a linear or branched alkyl group having 1 to 4 carbon atoms, each of $R^7$ to $R^{10}$ is independently a linear or branched alkyl group having 1 to 4 carbon atoms, and n is an integer of from 1 to 3;

[Chemical Formula 1]

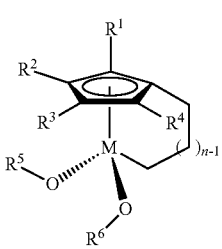

in the above Chemical Formula 1, M is Ti, Zr or Hf, each of $R^1$ to $R^4$ is independently hydrogen or a linear or branched alkyl group having 1 to 4 carbon atoms, each of $R^5$ and $R^6$ is independently a linear or branched alkyl group having 1 to 4 carbon atoms, and n is an integer of from 1 to 3.

According to a third aspect of the present disclosure, there is provided a method of preparing a Group 4 metal element-containing compound, represented by the following Chemical Formula 1, including reacting a compound represented by the following Chemical Formula 3 with M'OR$^5$ and/or M'OR$^6$ as an alkali metal salt of linear or branched alcohol having 1 to 4 carbon atoms:

[Chemical Formula 3]

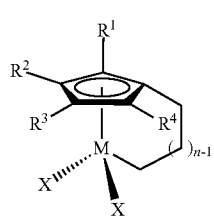

in the above Chemical Formula 3, M is Ti, Zr or Hf, each of $R^1$ to $R^4$ is independently hydrogen or a linear or branched alkyl group having 1 to 4 carbon atoms, X is a halogen, and n is an integer of from 1 to 3;

[Chemical Formula 1]

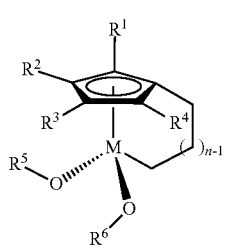

in the above Chemical Formula 1, M is Ti, Zr or Hf, each of $R^1$ to $R^4$ is independently hydrogen or a linear or branched alkyl group having 1 to 4 carbon atoms, each of $R^5$ and $R^6$ is independently a linear or branched alkyl group having 1 to 4 carbon atoms, and n is an integer of from 1 to 3.

According to a fourth aspect of the present disclosure, there is provided a precursor composition for depositing a film, including a Group 4 metal element-containing compound according to the first aspect of the present disclosure.

According to a fifth aspect of the present disclosure, there is provided a method of depositing a Group 4 metal element-containing film, including forming a Group 4 metal element-containing film using a precursor composition for depositing a film according to the fourth aspect of the present disclosure.

Effects of the Invention

According to exemplary embodiments of the present disclosure, a Group 4 metal element-containing novel compound has a structure in which a carbon directly bonded to a Group 4 central metal is connected to a cyclopentadienyl group coordinated at the central metal through an alkylene chain and is a novel compound which has not been conventionally known in the art.

The Group 4 metal element-containing novel compounds according to exemplary embodiments of the present disclosure have high thermal stability and thus can be used as a precursor for atomic layer deposition or chemical vapor deposition to form a Group 4 metal element-containing film and particularly can be used to uniformly form a Group 4 metal element-containing film having a thickness of from several nm to several tens of nm on a substrate having a trench (groove) in its surface or porous substrate. For example, in a substrate having a fine trench (groove) with an aspect ratio of about 1 or more and a width of about 1 μm or less in its surface, the Group 4 metal element-containing novel compounds have an excellent effect of uniformly forming a Group 4 metal element-containing film having a thickness of several nm to several tens of nm on the entire surface of the substrate including a surface of the fine trench (groove) including a surface of the deepest portion of the fine trench (groove) and an upper surface of the fine trench (groove).

According to exemplary embodiments of the present disclosure, a method of preparing a Group 4 metal element-containing film can be applied to manufacturing commercial semiconductor devices. Particularly, in order to manufacture a DRAM semiconductor device, it is necessary to form a high-k material to a thickness of several nm on a substrate having a trench with a width of much less than 100 nm or 50 nm and an aspect ratio of 10:1, 20:1, or 30:1, or a deeper and narrower trench. Particularly, it is necessary to form a high-k material having a uniform thickness even at a temperature of about 250° C., 280° C., 300° C., or more, and, thus, a precursor composition with which a film having a uniform thickness can be formed on a very narrow and deep trench by atomic layer deposition (ALD) even at a high temperature is needed and thus a Ti, Zr, or Hf compound having very high thermal stability is needed to be used as the precursor composition.

The Group 4 metal element-containing compound according to exemplary embodiments of the present disclosure can be used as a precursor used for ALD, CVD, and the like and thus can provide properties, e.g., improved thermal stability, high volatility and/or increased deposition rate, required for manufacturing next-generation devices such as semiconductors and therefore can be usefully utilized for forming a Group 4 metal element-containing film or thin film.

Further, the Group 4 metal element-containing compound according to exemplary embodiments of the present disclosure can be applied in various fields such as catalyst and the like.

BEST MODE FOR CARRYING OUT THE INVENTION

Figure 1:
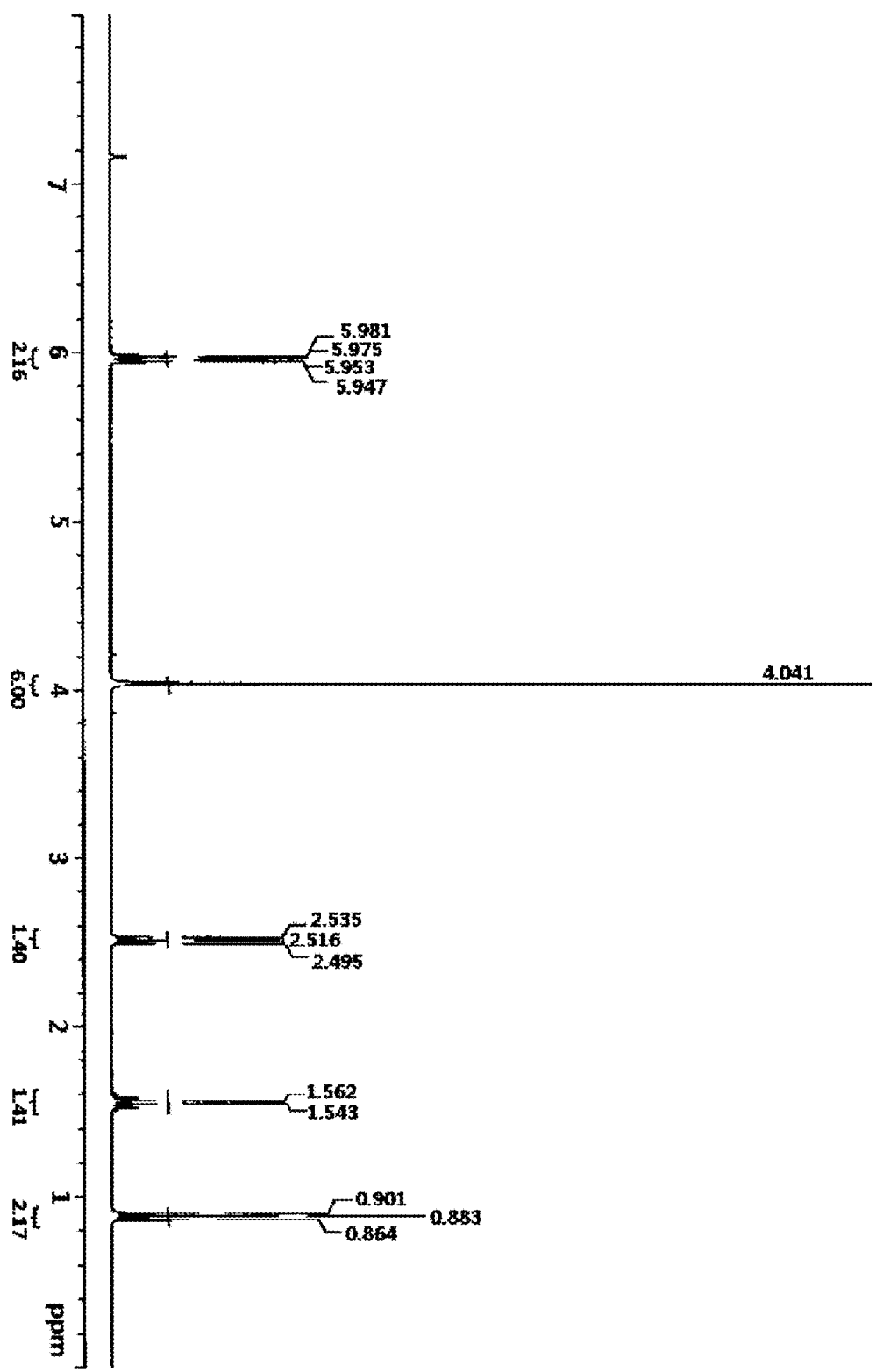
FIG. 1 is a H$^1$-HMR spectrum of Cp(CH$_2$)$_3$Ti(OCH$_3$)$_2$ prepared in accordance with an example of the present disclosure.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "alkyl" includes linear or branched alkyl groups having 1 to 12 carbon atoms, 1 to 10 carbon atoms, 1 to 8 carbon atoms, 1 to 5 carbon atoms, or 1 to 4 carbon atoms and all the possible isomers thereof. For example, the alkyl group may include methyl group (Me), ethyl group (Et), n-propyl group ($^n$Pr), iso-propyl group ($^i$Pr), n-butyl group ($^n$Bu), tert-butyl group ($^t$Bu), iso-butyl group ($^i$Bu), sec-butyl group ($^s$Bu), pentyl group, hexyl group, iso-hexyl group, heptyl group, 4,4-dimethyl pentyl group, octyl group, 2,2,4-trimethyl pentyl group, nonyl group, decyl group, undecyl group, dodecyl group, and isomers thereof, but may not be limited thereto.

Through the whole document, the term "Group 4 metal element" refers to a chemical element belonging to the fourth group in the Periodic Table and may include Ti, Zr or Hf.

Through the whole document, the term "Cp" is the abbreviation of a "cyclopentadienyl" group.

Through the whole document, the term "halogen" or "halo" refers to fluorine (F), chlorine (Cl), bromine (Br), or iodine (I).

In the following description, exemplary embodiments of the present disclosure will be described in detail, but the present disclosure may not be limited thereto.

According to a first aspect of the present disclosure, there is provided a Group 4 metal element-containing compound, represented by the following Chemical Formula 1:

[Chemical Formula 1]

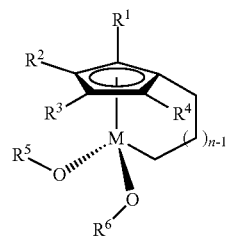

in the above Chemical Formula 1, M is Ti, Zr or Hf, each of $R^1$ to $R^4$ is independently hydrogen or a linear or branched alkyl group having 1 to 4 carbon atoms, each of $R^5$ and $R^6$ is independently a linear or branched alkyl group having 1 to 4 carbon atoms, and n is an integer of from 1 to 3.

In an exemplary embodiment of the present disclosure, in the above Chemical Formula 1, M may be Ti, Zr or Hf and each of $R^5$ and $R^6$ may be independently methyl, ethyl, n-propyl, iso-propyl, n-butyl, iso-butyl, sec-butyl, or tert-butyl, but may not be limited thereto.

In an exemplary embodiment of the present disclosure, in the above Chemical Formula 1, $R^5$ and $R^6$ may be identical to or different to each other.

In an exemplary embodiment of the present disclosure, in the above Chemical Formula 1, M may be Ti, Zr or Hf, each of $R^5$ and $R^6$ may be independently CH$_3$, C$_2$H$_5$ or CH(CH$_3$)$_2$, and n may be from 1 to 3, or may be 2, but may not be limited thereto.

In an exemplary embodiment of the present disclosure, in the above Chemical Formula 1, M may be Ti, Zr or Hf, $R^5$ and $R^6$ may be CH$_3$, and n may be from 1 to 3, or may be 2, but may not be limited.

In an exemplary embodiment of the present disclosure, the Group 4 metal element-containing compound represented by the above Chemical Formula 1 may include compounds represented as the following structures, but may not be limited thereto:

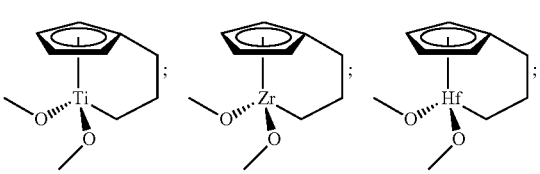

-continued

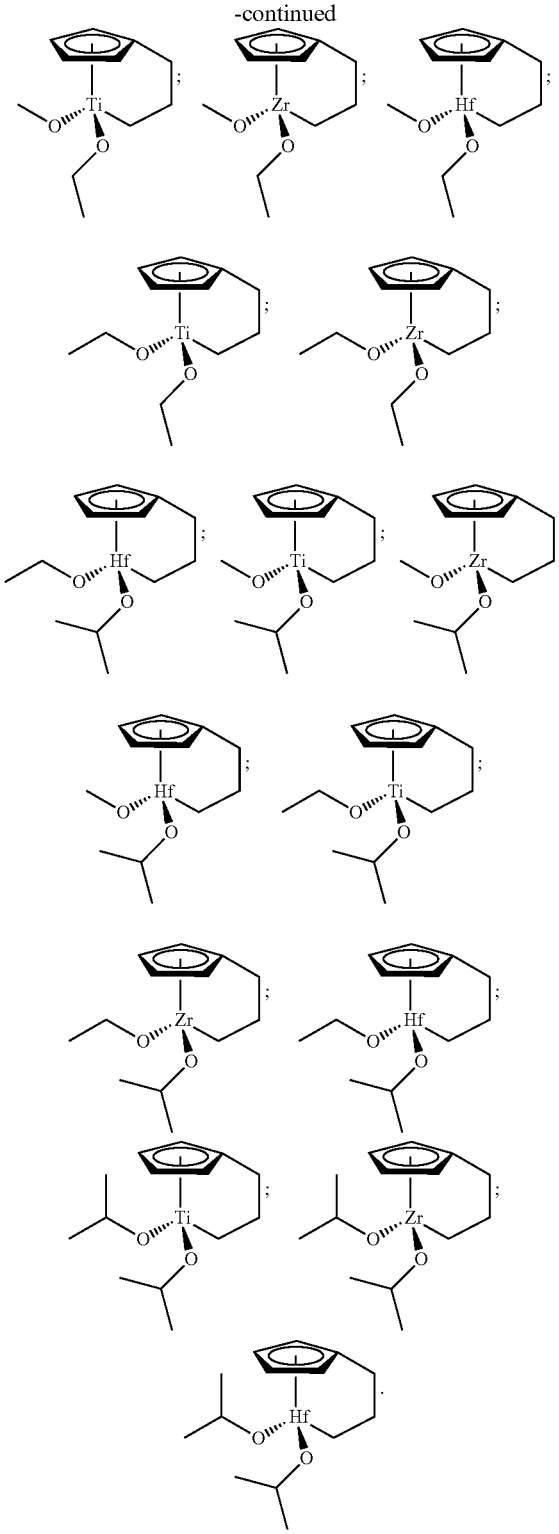

According to a second aspect of the present disclosure, there is provided a method of preparing a Group 4 metal element-containing compound, represented by the following Chemical Formula 1, including reacting a compound represented by the following Chemical Formula 2 with linear or branched alcohol as $R^5OH$ and/or $R^6OH$ having 1 to 4 carbon atoms:

[Chemical Formula 2]

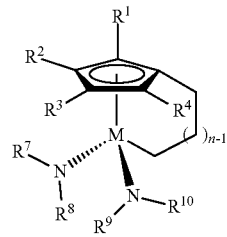

in the above Chemical Formula, M is Ti, Zr or Hf, each of $R^1$ to $R^4$ is independently hydrogen or a linear or branched alkyl group having 1 to 4 carbon atoms, each of $R^7$ to $R^{10}$ is independently a linear or branched alkyl group having 1 to 4 carbon atoms, and n is an integer of from 1 to 3;

[Chemical Formula 1]

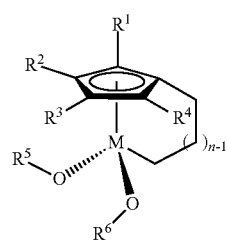

in the above Chemical Formula 1, M is Ti, Zr or Hf, each of $R^1$ to $R^4$ is independently hydrogen or a linear or branched alkyl group having 1 to 4 carbon atoms, each of $R^5$ and $R^6$ is independently a linear or branched alkyl group having 1 to 4 carbon atoms, and n is an integer of from 1 to 3.

In an exemplary embodiment of the present disclosure, in the above Chemical Formula 1, M may be Ti, Zr or Hf and each of $R^5$ and $R^6$ may be independently methyl, ethyl, n-propyl, iso-propyl, n-butyl, iso-butyl, sec-butyl, or tert-butyl, but may not be limited thereto.

In an exemplary embodiment of the present disclosure, in the above Chemical Formula 1, $R^5$ and $R^6$ may be identical to or different from each other. For example, if $R^5$ and $R^6$ are different to each other, $R^5OH$ and $R^6OH$ may be simultaneously or sequentially added to and reacted with a compound represented by the above Chemical Formula 2.

In an exemplary embodiment of the present disclosure, in the above Chemical Formula 1, M may be Ti, Zr or Hf, each of $R^5$ and $R^6$ may be independently $CH_3$, $C_2H_5$ or $CH(CH_3)_2$, and n may be from 1 to 3, or may be 2, but may not be limited thereto.

In an exemplary embodiment of the present disclosure, in the above Chemical Formula 1, M may be Ti, Zr or Hf, $R^5$ and $R^6$ may be $CH_3$, and n may be from 1 to 3, or may be 2, but may not be limited.

In an exemplary embodiment of the present disclosure, a Group 4 metal element-containing compound represented by the above Chemical Formula 1 refers to compounds represented by Chemical Formula 1 and specifically the exemplified compounds therefor in the first aspect of the present disclosure, but may not be limited thereto.

According to a third aspect of the present disclosure, there is provided a method of preparing a Group 4 metal element-containing compound, represented by the following Chemical Formula 1, including reacting a compound represented by the following Chemical Formula 3 with M'OR⁵ and/or M'OR⁶ as a salt of an alkali metal M' of linear or branched alcohol having 1 to 4 carbon atoms:

[Chemical Formula 3]

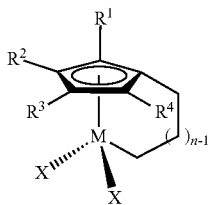

in the above Chemical Formula 3, M is Ti, Zr or Hf, each of $R^1$ to $R^4$ is independently hydrogen or a linear or branched alkyl group having 1 to 4 carbon atoms, X is a halogen, and n is an integer of from 1 to 3;

[Chemical Formula 1]

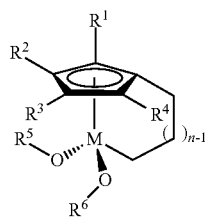

in the above Chemical Formula 1, M is Ti, Zr or Hf, each of $R^1$ to $R^4$ is independently hydrogen or a linear or branched alkyl group having 1 to 4 carbon atoms, each of $R^5$ and $R^6$ is independently a linear or branched alkyl group having 1 to 4 carbon atoms, and n is an integer of from 1 to 3.

In an exemplary embodiment of the present disclosure, in the above Chemical Formula 1, M may be Ti, Zr or Hf and each of $R^5$ and $R^6$ may be independently methyl, ethyl, n-propyl, iso-propyl, n-butyl, iso-butyl, sec-butyl, or tert-butyl, but may not be limited thereto.

In an exemplary embodiment of the present disclosure, in the above Chemical Formula 1, $R^5$ and $R^6$ may be identical to or different from each other. For example, if $R^5$ and $R^6$ are different from each other, M'OR⁵ and M'OR⁶ may be simultaneously or sequentially added to and reacted with a compound represented by the above Chemical Formula 2.

In an exemplary embodiment of the present disclosure, in the above Chemical Formula 1, M may be Ti, Zr or Hf, each of $R^5$ and $R^6$ may be independently $CH_3$, $C_2H_5$ or $CH(CH_3)_2$, and n may be from 1 to 3 or may be 2, but may not be limited thereto.

In an exemplary embodiment of the present disclosure, in the above Chemical Formula 1, M may be Ti, Zr or Hf, $R^5$ and $R^6$ may be $CH_3$, and n may be from 1 to 3 or may be 2, but may not be limited thereto.

In an exemplary embodiment of the present disclosure, a Group 4 metal element-containing compound represented by the above Chemical Formula 1 refers to compounds represented by Chemical Formula 1 and specifically exemplified compounds therefor in the first aspect of the present disclosure, but may not be limited thereto.

In an exemplary embodiment of the present disclosure, each of the alkali metal salts M'OR⁵ and M'OR⁶ of the alcohol may be independently, e.g., methoxylithium (LiOMe), ethoxylithium (LiOEt), isopropoxylithium (LiO$^i$Pr), methoxysodium (NaOMe), ethoxysodium (NaOEt), iso-propoxysodium (NaO$^i$Pr), methoxypotassium (KOMe), ethoxypotassium (KOEt), or isopropoxypotassium (KO$^i$Pr), but may not be limited thereto.

According to a fourth aspect of the present disclosure, there is provided a precursor composition for depositing a film, including a Group 4 metal element-containing compound according to the first aspect of the present disclosure.

According to a fifth aspect of the present disclosure, there is provided a method of depositing a Group 4 metal element-containing film, including forming a Group 4 metal element-containing film using a precursor composition for depositing a film according to the fourth aspect of the present disclosure.

The Group 4 metal element-containing compound according to the first aspect of the present disclosure and used in the precursor composition for depositing a film according to the fourth aspect of the present disclosure and the method of depositing a Group 4 metal element-containing film according to the fifth aspect of the present disclosure is represented by the following Chemical Formula 1:

[Chemical Formula 1]

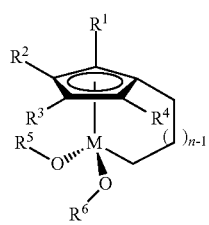

in the above Chemical Formula 1, M is Ti, Zr or Hf, each of $R^1$ to $R^4$ is independently hydrogen or a linear or branched alkyl group having 1 to 4 carbon atoms, each of $R^5$ and $R^6$ is independently a linear or branched alkyl group having 1 to 4 carbon atoms, and n is an integer of from 1 to 3.

In an exemplary embodiment of the present disclosure, in the above Chemical Formula 1, M may be Ti, Zr or Hf and each of $R^5$ and $R^6$ may be independently methyl, ethyl, n-propyl, iso-propyl, n-butyl, iso-butyl, sec-butyl, or tert-butyl, but may not be limited thereto.

In an exemplary embodiment of the present disclosure, in the above Chemical Formula 1, $R^5$ and $R^6$ may be identical to or different from each other.

In an exemplary embodiment of the present disclosure, in the above Chemical Formula 1, M may be Ti, Zr or Hf each of $R^5$ and $R^6$ may be independently $CH_3$, $C_2H_5$ or $CH(CH_3)_2$, and n may be from 1 to 3, or may be 2, but may not be limited thereto.

In an exemplary embodiment of the present disclosure, in the above Chemical Formula 1, M may be Ti, Zr or Hf, $R^5$ and $R^6$ may be $CH_3$, and n may be from 1 to 3, or may be 2, but may not be limited thereto.

In an exemplary embodiment of the present disclosure, the Group 4 metal element-containing compound represented by the above Chemical Formula 1 may include compounds represented as the following structures, but may not be limited thereto:

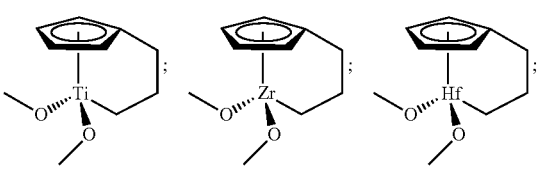

-continued

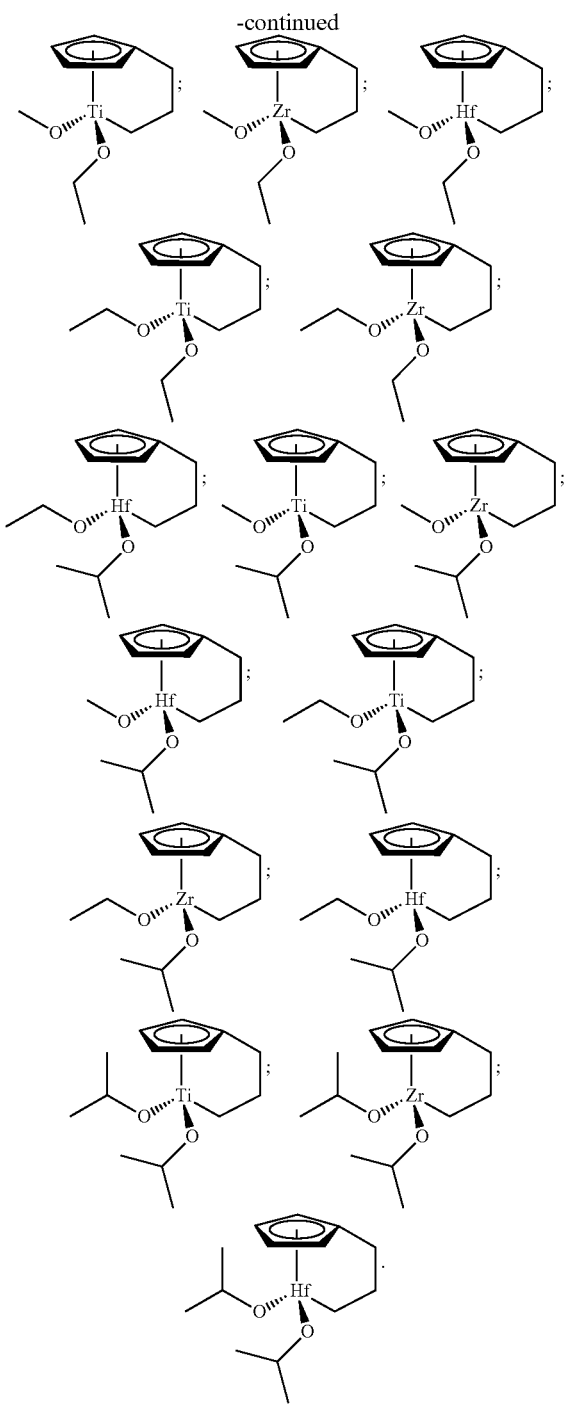

In an exemplary embodiment of the present disclosure, the precursor composition for depositing a film may be used for deposition of a Group 4 metal element-containing film or thin film. The Group 4 metal element-containing film or thin film may have a thickness of from about 1 nm to several μm, but may not be limited thereto.

In an exemplary embodiment of the present disclosure, the Group 4 metal element-containing film or thin film may include a film or thin film containing a metal of Ti, Zr and/or Hf, a film or thin film containing an oxide of Ti, Zr and/or Hf, a film or thin film containing a nitride of Ti, Zr and/or Hf, a film or thin film containing an oxynitride of Ti, Zr and/or Hf, or a film or thin film containing a carbonitride of Ti, Zr and/or Hf, but may not be limited thereto.

In an exemplary embodiment of the present disclosure, the Group 4 metal element-containing film or thin film may be used as a high-k film in a semiconductor device, a catalyst, or the like, but may not be limited thereto.

In an exemplary embodiment of the present disclosure, a method of depositing a Group 4 metal element-containing film or thin film may include forming a Group 4 metal element-containing film or thin film by supplying and depositing the precursor composition to form a Group 4 metal element-containing film or thin film on a substrate positioned in a deposition chamber, but may not be limited thereto. The method of depositing a film may employ a method and an apparatus known in the art and may be performed using one or more additional reaction gases together if necessary. The substrate may employ a silicon semiconductor wafer and a compound semiconductor wafer, but may not be limited thereto. A substrate having a hole or trench may be used, and for example, a porous substrate having a large surface area may be used as a catalyst.

In an exemplary embodiment of the present disclosure, the deposition of a film may be performed by metal organic chemical vapor deposition (MOCVD) or atomic layer deposition (ALD), but may not be limited thereto. The metal organic chemical vapor deposition (MOCVD) or atomic layer deposition (ALD) may be performed using a deposition apparatus, deposition conditions, and additional reaction gases known in the art.

Specifically, according to the precursor composition for depositing a film according to the fourth aspect of the present disclosure and the method of depositing a Group 4 metal element-containing film or thin film according to the fifth aspect of the present disclosure including forming a Group 4 metal element-containing film or thin film using the precursor composition for depositing a film, the Group 4 metal element-containing novel compounds according to an exemplary embodiment of the present disclosure which are included in the precursor composition for depositing a film have high thermal stability and thus can be used as a precursor for atomic layer deposition or chemical vapor deposition to form a Group 4 metal element-containing film and particularly can be used to uniformly form a Group 4 metal element-containing film having a thickness of from several nm to several tens of nm on a substrate having a trench (groove) in its surface or porous substrate. For example, in a substrate having a fine trench (groove) in its surface with an aspect ratio of about 1 or more, 2 or more, 5 or more, 10 or more, 20 or more, 30 or more or 40 or more and a width of about 1 μm or less, 500 nm or less, 400 nm or less, 300 nm or less, 200 nm or less, 100 nm or less, 80 nm or less, 60 nm or less, 50 nm or less, 40 nm or less, 30 nm or less, 20 nm or less or 10 nm or less in its surface, the Group 4 metal element-containing novel compounds have an excellent effect of uniformly forming a Group 4 metal element-containing film having a thickness of from several nm to several tens of nm on the entire surface of the substrate including a surface of the fine trench (groove) including a surface of the deepest portion of the fine trench (groove) and an upper surface of the fine trench (groove). For example, the thickness of from several nm to several tens of nm may be about 50 nm or less, about 40 nm or less, about 30 nm or less, about 20 nm or less, about 10 nm or less, from about 1 nm to about 10 nm, from about 1 nm to about 20 nm, from about 1 nm to about 30 nm, from about 1 nm to about 40 nm, or from about 1 nm to about 50 nm, but may not be limited thereto.

The precursor composition for depositing a film according to the fourth aspect of the present disclosure and the method of depositing a Group 4 metal element-containing film or thin film according to the fifth aspect of the present disclosure including forming a Group 4 metal element-containing film or thin film using the precursor composition for depositing a film can be applied to manufacturing commercial semiconductor devices. Particularly, in order to manufacture a DRAM semiconductor device, it is necessary to form a high-k material to a thickness of several nm on a substrate having a trench with a width of much less than 100 nm or 50 nm and an aspect ratio of 10:1, 20:1, or 30:1, or a deeper and narrower trench. Particularly, it is necessary to form a high-k material having a uniform thickness even at a temperature of about 250° C., 280° C., 300° C., or more, and, thus, a precursor composition with which a film having a uniform thickness can be formed on a very narrow and deep trench by atomic layer deposition (ALD) even at a high temperature is needed and a Ti, Zr, or Hf compound having very high thermal stability is needed to be used as the precursor composition, and therefore, the precursor composition for depositing a film according to the fourth aspect of the present disclosure and the method of depositing a Group 4 metal element-containing film or thin film according to the fifth aspect of the present disclosure including forming a Group 4 metal element-containing film or thin film using the precursor composition for depositing a film can be usefully utilized.

MODE FOR CARRYING OUT THE INVENTION

Hereinafter, the present disclosure will be explained in more detail with reference to Examples. However, the following Examples are illustrative only for better understanding of the present disclosure but do not limit the present disclosure.

EXAMPLES

<Preparation Example 1> Preparation of Cp(CH$_2$)$_3$MgCl

After 11.2 g (0.462 mol, 3 equivalents) of magnesium and 100 mL of tetrahydrofuran (THF, C$_4$H$_8$O) were put into a flame-dried 1 L Schlenk flask, the flask was maintained at room temperature. After 21.8 g (0.154 mol, 1 equivalent) of 3-chloro-propylcyclopentadiene was added to the flask, the obtained reaction solution was stirred for 15 hours while the temperature was slowly increased to 50° C. Then, the temperature of the flask was slowly decreased to room temperature and the reaction solution was filtered through a celite pad and a glass frit to remove excess magnesium, and, thus, Grignard reagent Cp(CH$_2$)$_3$MgCl was obtained from the obtained filtrate.

<Preparation Example 2> Preparation of Cp(CH$_2$)$_3$TiCl$_2$

After 99 g (0.522 mol, 1 equivalent) of titanium tetrachloride (TiCl$_4$) and 1,000 mL of toluene (C$_6$H$_5$—CH$_3$) were put into a flame-dried 3 L Schlenk flask, the flask was cooled at 10° C. After the Grignard reagent Cp(CH$_2$)$_3$MgCl (0.522 mol, 1 equivalent) prepared in Preparation Example 1 and 53 g (0.522 mol, 1 equivalent) of triethylamine were diluted in 500 mL of toluene and slowly drop-wisely added to the flask, the obtained reaction solution was refluxed for 15 hours.

After the reaction was completed, the solvent and volatile by-product were removed under a reduced pressure and washing was carried out with 200 mL of n-hexane three times and the reaction product was subject to a reduced pressure to remove the solvent and distilled under a reduced pressure, and, thus, 69 g (yield of 59%) of red solid compound Cp(CH$_2$)$_3$TiCl$_2$ represented as the following structure was obtained:

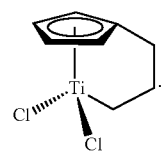

<Preparation Example 3> Preparation of Cp(CH$_2$)$_3$ZrCl$_2$ and Cp(CH$_2$)$_3$HfCl$_2$ The precursor Cp(CH$_2$)$_3$ZrCl$_2$ or Cp(CH$_2$)$_3$HfCl$_2$ was prepared by the same method as in Preparation Example 2 except that zirconium tetrachloride (ZrCl$_4$) or hafnium tetrachloride (HfCl$_4$) was used instead of titanium tetrachloride (TiCl$_4$) used in Preparation Example 2.

<Preparation Example 4> Preparation of Cp(CH$_2$)$_3$Ti[N(CH$_3$)$_2$]$_2$

After 277 g (1.044 mol, 2 equivalents) of an n-butyllithium hexane solution was put into a flame-dried 3 L Schlenk flask, the flask was cooled at −40° C. 47 g (1.044 mol, 2 equivalents) of dimethylamine was slowly dropwisely added to the flask and then stirred at room temperature for 3 hours. After Cp(CH$_2$)$_3$TiCl$_2$ (0.522 mol, 1 equivalent) prepared in Preparation Example 2 was slowly dropwisely added to the flask, the obtained reaction solution was stirred at 40° C. for 4 hours.

After the reaction was completed, the solvent and volatile by-product were removed under a reduced pressure and then extraction was carried out with 500 mL of n-hexane. After the n-hexane extract was filtered through a celite pad and a glass frit, the obtained filtrate was subject to a reduced pressure to remove the solvent and distilled under a reduced pressure, and, thus, 50 g (yield of 40%) of red liquid compound Cp(CH$_2$)$_3$Ti[N(CH$_3$)$_2$]$_2$ represented as the following structure was obtained:

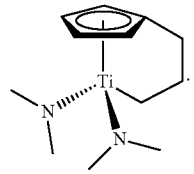

<Preparation Example 5> Preparation of Cp(CH$_2$)$_3$Zr[N(CH$_3$)$_2$]$_2$

After 41 g (0.154 mol, 1 equivalent) of tetrakis(dimethylamino)zirconium [Zr(N(CH$_3$)$_2$)$_4$] and 100 mL of n-hexane (C$_6$H$_{14}$) were put into a flame-dried 1 L Schlenk flask, the flask was maintained at room temperature. After Grignard reagent Cp(CH$_2$)$_3$MgCl (0.154 mol, 1 equivalent) prepared in Preparation Example 1 was slowly drop-wisely added to the flask, the obtained reaction solution was refluxed for 15 hours.

After the reaction was completed, the solvent and volatile by-product were removed under a reduced pressure and then extraction was carried out with 200 mL of n-hexane. After the n-hexane extract was filtered through a celite pad and a glass frit, the obtained filtrate was subject to a reduced pressure to remove the solvent and distilled under a reduced pressure, and, thus, 27 g (yield of 61%) of pale yellow liquid compound $Cp(CH_2)_3Zr[N(CH_3)_2]_2$ which is a liquid zirconium compound represented as the following structure was obtained:

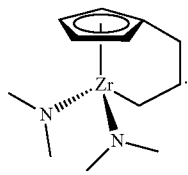

<Preparation Example 6> Preparation of $Cp(CH_2)_3$ $Hf[N(CH_3)_2]_2$

After 198 g (0.558 mol, 1 equivalent) of tetrakis(dimethylamino)hafnium $[Hf(N(CH_3)_2)_4]$ and 500 mL of n-hexane were put into a flame-dried 1 L Schlenk flask, the flask was maintained at room temperature. After Grignard reagent $Cp(CH_2)_3MgCl$ (0.558 mol, 1 equivalent) prepared in Preparation Example 1 was slowly drop-wisely added to the flask, the obtained reaction solution was refluxed for 15 hours.

After the reaction was completed, the solvent and volatile by-product were removed under a reduced pressure and then extraction was carried out with 1,000 mL of n-hexane. After the n-hexane extract was filtered through a celite pad and a glass frit, the obtained filtrate was subject to a reduced pressure to remove the solvent and distilled under a reduced pressure, and, thus, 108 g (yield of 52%) of pale yellow liquid compound $Cp(CH_2)_3Hf[N(CH_3)_2]_2$ represented as the following structure was obtained:

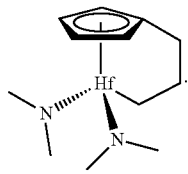

<Example 1> Preparation of $Cp(CH_2)_3Ti(OCH_3)_2$

After 35 g (0.145 mol, 1 equivalent) of $Cp(CH_2)_3Ti[N(CH_3)_2]_2$ prepared in Preparation Example 4 and 150 mL of n-hexane $(C_6H_{14})$ were put into a flame-dried 250 mL Schlenk flask, 9.3 g (0.290 mol, 2.1 equivalents) of methanol was slowly drop-wisely added to the flask and then stirred at room temperature for 2 hours.

Figure 2:
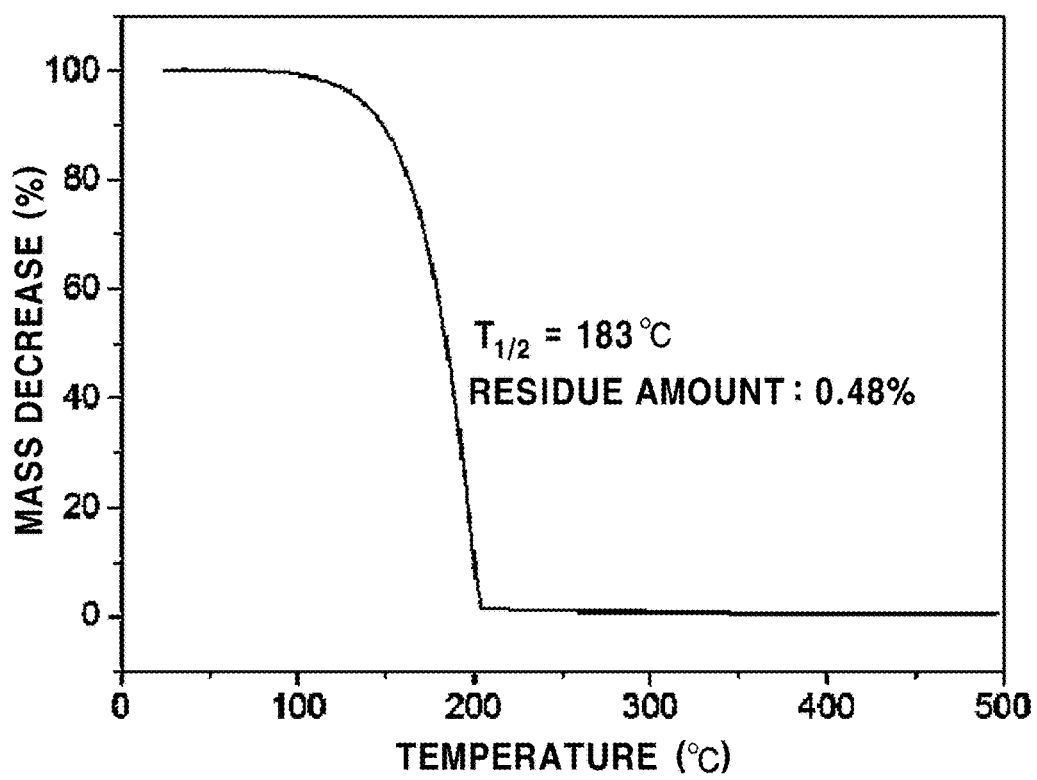
FIG. 2 is a thermogravimetric analysis graph for Cp(CH$_2$)$_3$Ti(OCH$_3$)$_2$ prepared in accordance with an example of the present disclosure and a compound according to a comparative example.
Figure 3:
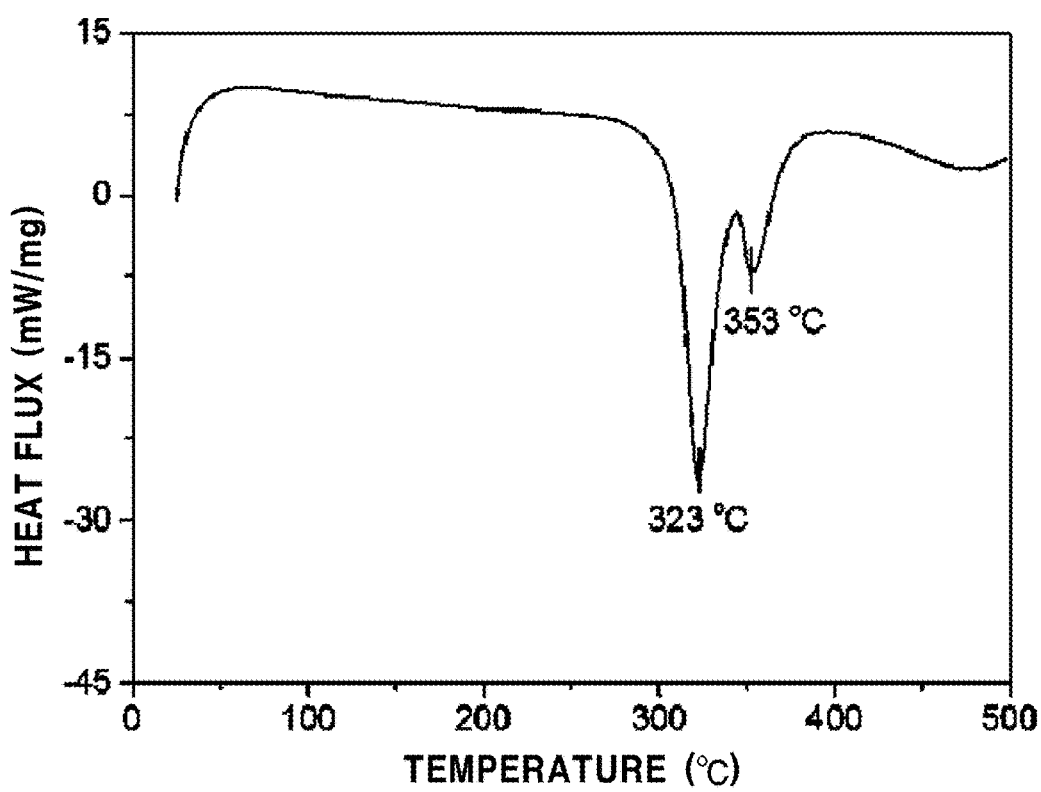
FIG. 3 is a differential scanning calorimetry analysis graph for Cp(CH$_2$)$_3$Ti(OCH$_3$)$_2$ prepared in accordance with an example of the present disclosure.

After the reaction was completed, the solvent and volatile by-product were removed under a reduced pressure and distilled under reduced pressure, and, thus, 15 g (yield of 50%) of pale yellow liquid compound $Cp(CH_2)_3Ti(OCH_3)_2$ represented as the following structure was obtained. A NMR spectrum of the obtained titanium liquid compound was as shown in FIG. 1, a thermogravimetric analysis graph therefor was as shown in FIG. 2 and a differential scanning calorimetry analysis graph therefor was as shown in FIG. 3:

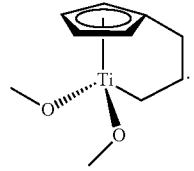

Boiling point (bp) 80° C. (0.25 torr);
Elemental analysis calcd for $C_{10}H_{16}O_2Ti$: C, 55.52, H, 7.44; found C, 55.58, H, 7.46;
1H-NMR (400 MHz, $C_6D_6$, 25): δ 5.989, 5.956 (m, 4H, $C_5\underline{H}_4$—$CH_2CH_2CH_2$), δ 4.045 (s, 6H, OC$\underline{H}_3$), δ 2.520 (t, 2H, $C_5H_4$—$CH_2CH_2C\underline{H}_2$), δ 1.566 (m, 2H, $C_5H_4$—$CH_2C\underline{H}_2CH_2$), δ 0.887 (t, 2H, $C_5H_4$—$C\underline{H}_2CH_2CH_2$).

<Example 2> Preparation of $Cp(CH_2)_3Zr(OCH_3)_2$

After 10 g (0.035 mol, 1 equivalent) of $Cp(CH_2)_3Zr[N(CH_3)_2]_2$ prepared in Preparation Example 5 and 150 mL of n-hexane were put into a flame-dried 250 mL Schlenk flask, 2.4 g (0.074 mol, 2.1 equivalents) of methanol was slowly drop-wisely added to the flask and then stirred at room temperature for 2 hours.

After the reaction was completed, the solvent and volatile by-product were removed under a reduced pressure and distilled under a reduced pressure, and, thus, 3.6 g (yield of 40%) of pale yellow liquid compound $Cp(CH_2)_3Zr(OCH_3)_2$ represented as the following structure was obtained:

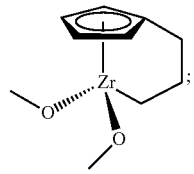

Boiling point (bp) 102° C. (0.2 torr);
Elemental analysis calcd for $C_{10}H_{16}O_2Zr$: C, 46.29, H, 6.22; found C, 46.28, H, 6.24;
1H-NMR (400 MHz, $C_6D_6$, 25): δ 5.885, 5.869 (m, 4H, $C_5\underline{H}_4$—$CH_2CH_2CH_2$), δ 3.878 (s, 6H, OC$\underline{H}$3), δ 2.460 (t, 2H, $C_5H_4$—$CH_2CH_2C\underline{H}_2$), δ 1.583 (m, 2H, $C_5H_4$—$CH_2C\underline{H}_2CH_2$), δ 0.939 (t, 2H, $C_5H_4$—$C\underline{H}_2CH_2CH_2$).

<Example 3> Preparation of $Cp(CH_2)_3Hf(OCH_3)_2$

After 10 g (0.027 mol, 1 equivalent) of $Cp(CH_2)_3Hf[N(CH_3)_2]_2$ prepared in Preparation Example 6 and 150 mL of n-hexane were put into a flame-dried 250 mL Schlenk flask, 2.4 g (0.056 mol, 2.1 equivalents) of methanol was slowly drop-wisely added to the flask and then stirred at room temperature for 2 hours.

After the reaction was completed, the solvent and volatile by-product were removed under a reduced pressure and distilled under a reduced pressure, and, thus, 3 g (yield of 32%) of yellow liquid compound $Cp(CH_2)_3Hf(OCH_3)_2$ represented as the following structure was obtained:

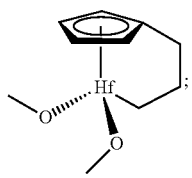

Boiling point (bp) 107° C. (0.2 torr);
Elemental analysis calcd for $C_{10}H_{16}O_2Hf$: C, 34.64, H, 4.65; found C, 34.60, H, 4.63;
1H-NMR (400 MHz, $C_6D_6$, 25): δ 5.743, 5.723 (m, 4H, $C_5\underline{H}_4$—$CH_2CH_2CH_2$), δ 3.815 (s, 6H, $OC\underline{H}_3$), δ 2.515 (t, 2H, $C_5H_4$—$CH_2CH_2C\underline{H}_2$), δ 1.503 (m, 2H, $C_5H_4$—$CH_2C\underline{H}_2CH_2$), δ 0.873 (t, 2H, $C_5H_4$—$C\underline{H}_2CH_2CH_2$).

<Example 4> Preparation of $Cp(CH_2)_3Zr(OCH_3)_2$ Using $Cp(CH_2)_3ZrCl_2$

After 68.7 g (0.257 mol, 2 equivalents) of an n-butyllithium hexane solution was put into a flame-dried 1 L Schlenk flask, the flask was cooled at −40° C. 8.3 g (0.257 mol, 2 equivalents) of methanol was slowly drop-wisely added to the flask and then stirred at room temperature for 3 hours. After $Cp(CH_2)_3ZrCl_2$ (0.129 mol, 1 equivalent) prepared in Preparation Example 3 was slowly drop-wisely added to the flask, the obtained reaction solution was stirred at 40° C. for 4 hours.

After the reaction was completed, the solvent and volatile by-product were removed under a reduced pressure and then extraction was carried out with 500 mL of n-hexane. After the n-hexane extract was filtered through a celite pad and a glass frit, the obtained filtrate was subject to a reduced pressure to remove the solvent and distilled under a reduced pressure, and, thus, 14 g (yield of 42%) of yellow liquid compound $Cp(CH_2)_3Zr(OCH_3)_2$ represented as the following structure was obtained:

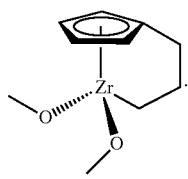

<Example 5> Preparation of $Cp(CH_2)_3Hf(OCH_3)_2$ Using $Cp(CH_2)_3HfCl_2$

After 50 g (0.187 mol, 2 equivalents) of an n-butyllithium hexane solution was put into a flame-dried 1 L Schlenk flask, cooling was carried out at −40° C. 6 g (0.187 mol, 2 equivalents) of methanol was slowly drop-wisely added to the flask and then stirred at room temperature for 3 hours. After $Cp(CH_2)_3HfCl_2$ (0.094 mol, 1 equivalent) prepared in Preparation Example 3 was slowly drop-wisely added to the flask, the obtained reaction solution was stirred at 40° C. for 4 hours.

After the reaction was completed, the solvent and volatile by-product were removed under a reduced pressure and then extraction was carried out with 500 mL of n-hexane. After the n-hexane extract was filtered through a celite pad and a glass frit, the obtained filtrate was subject to a reduced pressure to remove the solvent and distilled under a reduced pressure, and, thus, 11 g (yield of 34%) of yellow liquid compound $Cp(CH_2)_3Hf(OCH_3)_2$ represented as the following structure which is the same as that of the compound prepared in Example 3 was obtained:

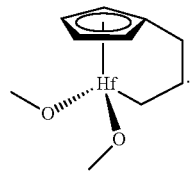

<Example 6> Preparation of $Cp(CH_2)_3Ti[OCH(CH_3)_2]_2$

After 35 g (0.145 mol, 1 equivalent) of $Cp(CH_2)_3Ti[N(CH_3)_2]_2$ prepared in Preparation Example 4 and 150 mL of n-hexane were put into a flame-dried 250 mL Schlenk flask, 17.5 g (0.290 mol, 2.1 equivalents) of isopropanol was slowly drop-wisely added to the flask and then stirred at room temperature for 2 hours.

After the reaction was completed, the solvent and volatile by-product were removed under a reduced pressure and distilled under a reduced pressure, and, thus, 17.7 g (yield of 45%) of pale yellow liquid compound $Cp(CH_2)_3Ti[OCH(CH_3)_2]_2$ represented as the following structure was obtained.

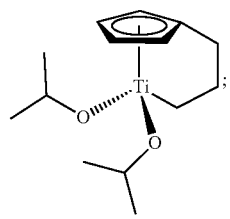

Boiling point (bp) 90° C. (0.3 torr);
Elemental analysis calcd for $C_{14}H_{24}O_2Ti$: C, 61.77, H, 8.89; found C, 61.78, H, 8.88;
1H-NMR (400 MHz, $C_6D_6$, 25° C.): δ 6.069, 6.022 (m, 4H, $C_5\underline{H}_4$—$CH_2CH_2CH_2$), δ 4.573 (m, 2H, $OC\underline{H}(CH_3)_2$), δ 2.621 (t, 2H, $C_5H_4$—$CH_2CH_2C\underline{H}_2$), δ 1.656 (m, 2H, $C_5H_4$—$CH_2C\underline{H}_2CH_2$), δ 1.195 (d, 12H, $OCH(C\underline{H}_3)_2$), δ 0.975 (t, 2H, $C_5H_4$—$C\underline{H}_2CH_2CH_2$).

<Example 7> Preparation of $Cp(CH_2)_3Hf[OCH(CH_3)_2]_2$

Synthesis I:
After 50 g (0.187 mol, 2 equivalents) of an n-butyllithium hexane solution was put into a flame-dried 1 L Schlenk flask, the flask was cooled at −40° C. 11.3 g (0.187 mol, 2 equivalents) of isopropanol was slowly drop-wisely added to the flask and then stirred at room temperature for 3 hours. After $Cp(CH_2)_3HfCl_2$ (0.094 mol, 1 equivalent) prepared in Preparation Example 3 was slowly drop-wisely added to the flask, the obtained reaction solution was stirred at 40° C. for 4 hours. After the reaction was completed, the solvent and volatile by-product were removed under a reduced pressure and then extraction was carried out with 500 mL of n-hexane. After the n-hexane extract was filtered through a celite pad and a glass frit, the obtained filtrate was subject to a reduced pressure to remove the solvent and distilled under a reduced pressure, and, thus, 12.5 g (yield of 33%) of yellow liquid compound $Cp(CH_2)_3Hf[OCH(CH_3)_2]_2$ represented as the following structure was obtained.

Synthesis II: After 10 g (0.035 mol, 1 equivalent) of $Cp(CH_2)_3Hf[N(CH_3)_2]_2$ prepared in Preparation Example 6 and 150 mL of n-hexane were put into a flame-dried 250 mL Schlenk flask, 4.5 g (0.074 mol, 2.1 equivalents) of isopropanol was slowly drop-wisely added to the flask and then stirred at room temperature for 2 hours. After the reaction was completed, the solvent and volatile by-product were removed under a reduced pressure and distilled under a reduced pressure, and, thus, 4.5 g (yield of 32%) of yellow liquid compound $Cp(CH_2)_3Hf[OCH(CH_3)_2]_2$ represented as the following structure was obtained.

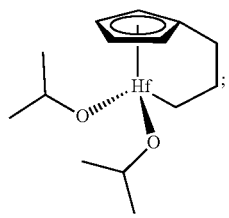

Boiling point (bp) 110° C. (0.3 torr);
Elemental analysis calcd for $C_{14}H_{24}O_2Hf$: C, 41.74, H, 6.01; found C, 41.72, H, 6.00;
1H-NMR (400 MHz, $C_6D_6$, 25): δ 6.183, 6.134 (m, 4H, $C_5\underline{H}_4$—$CH_2CH_2CH_2$), δ 4.359 (m, 2H, $OC\underline{H}(CH_3)_2$), δ 2.627 (t, 2H, $C_5H_4$—$CH_2CH_2C\underline{H}_2$), δ 1.641 (m, 2H, $C_5H_4$—$CH_2C\underline{H}_2CH_2$), δ 1.197 (d, 12H, $OCH(C\underline{H}_3)_2$), δ 0.931 (t, 2H, $C_5H_4$—$C\underline{H}_2CH_2CH_2$).

Figure 4:
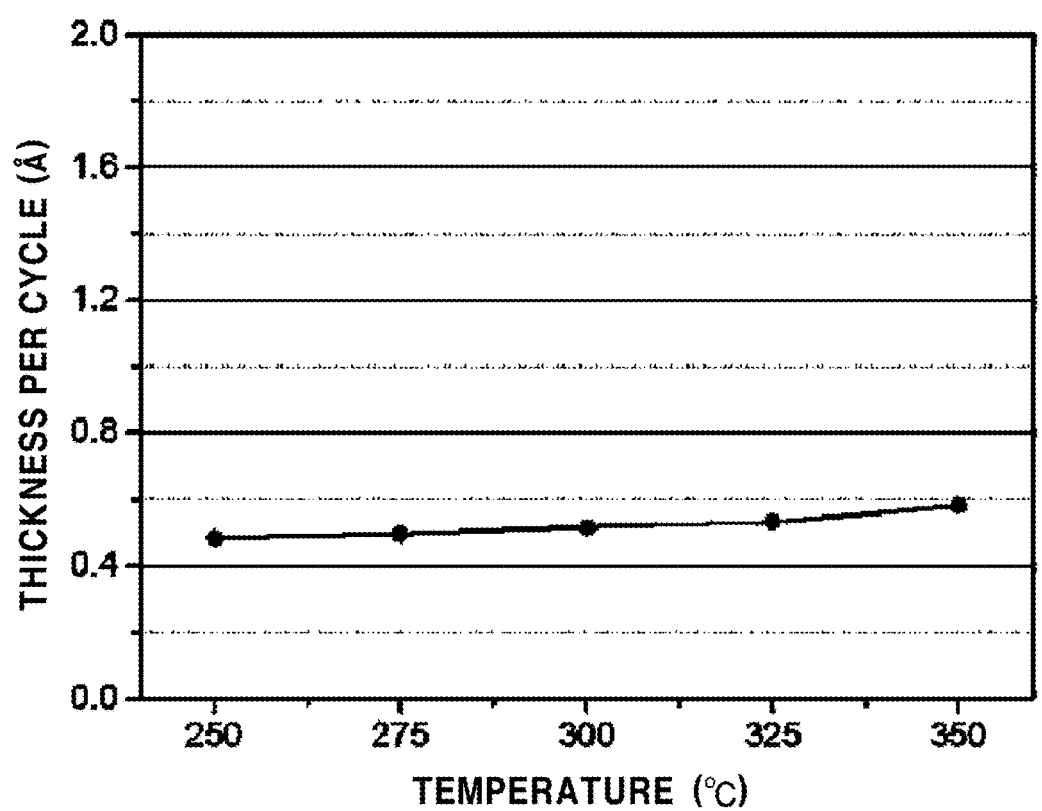
FIG. 4 shows film growth by atomic layer deposition using Cp(CH$_2$)$_3$Ti(OCH$_3$)$_2$ prepared in accordance with an example of the present disclosure, depending on a substrate temperature.

<Example 8> Formation of Titanium Oxide Film by Atomic Layer Deposition Using $Cp(CH_2)_3Ti(OCH_3)_2$ Compound and Ozone ($O_3$) Gas A test for forming a titanium oxide film by atomic layer deposition (ALD) using $Cp(CH_2)_3Ti(OCH_3)_2$ prepared in Example 1 as a precursor and ozone ($O_3$) gas as a reaction gas was conducted. In this case, a silicon (Si) wafer was used as a substrate. The substrate was heated at from 250° C. to 350° C. Further, a precursor compound put in a stainless-steel container was heated at a temperature of 90° C., and the precursor compound was supplied to an ALD reactor for performing atomic layer deposition by allowing argon (Ar) gas to pass through the container at a flow rate of 60 sccm. An internal pressure in the ALD reactor was maintained at 3 torr. An ALD source supply cycle, in which after a gas of the precursor compound was supplied to the ALD reactor for 10 seconds, then, argon gas was supplied for 10 seconds and then, ozone ($O_3$) gas was supplied for 10 seconds and argon gas was supplied again for 10 seconds, was repeated 200 times. Film growth per source material supply cycle of the titanium oxide thin film formed according to the above-described process was as shown in FIG. 4. As shown in FIG. 4, it was observed that film growth per ALD source supply cycle was generally uniform at 0.05 nm/cycle in the range of substrate temperature of from 250° C. to 350° C.

Figure 5:
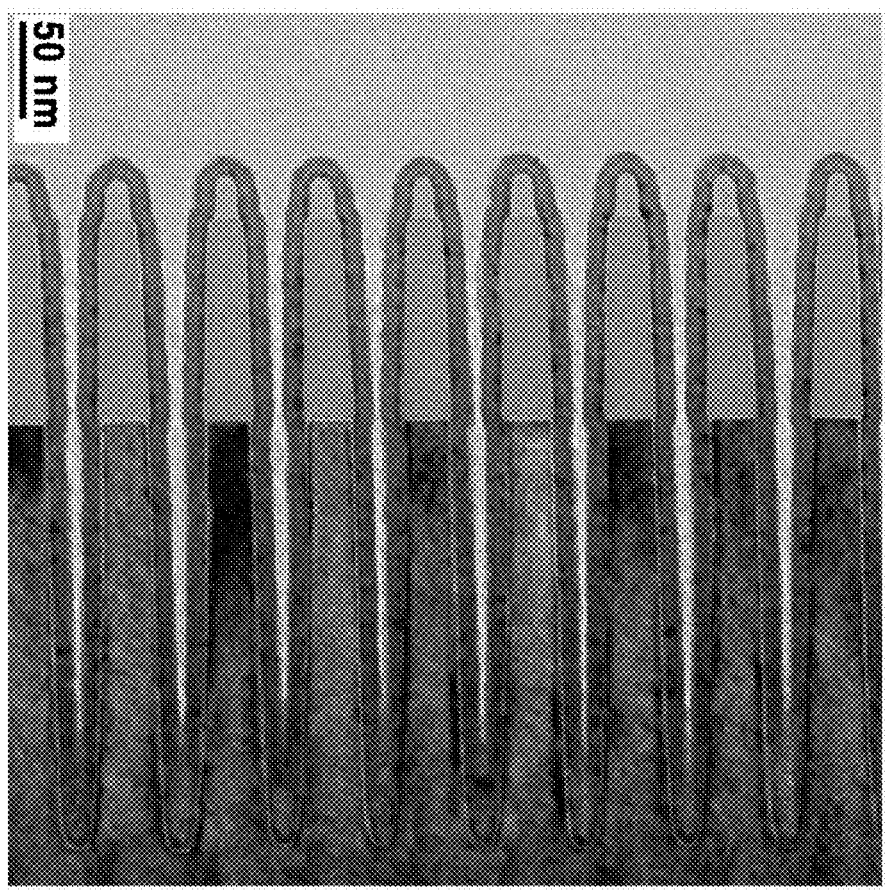
FIG. 5 shows a transmission electron microscope (TEM) observation result of a cross section of a film formed using Cp(CH$_2$)$_3$Ti(OCH$_3$)$_2$ prepared in accordance with an example of the present disclosure on a substrate including a fine trench.

FIG. 5 shows a transmission electron microscope (TEM) observation result of a cross section of a titanium oxide film formed by heating a substrate including fine trenches (grooves) with a width of about 55 nm and an aspect ratio of about 10:1 at 300° C. and repeating 98 times of the above-described ALD source supply cycle. It can be seen that a film having a uniform thickness of about 5 nm was formed on the entire surface of the substrate including a surface of the deepest portion of the trench and an upper surface of the trench in the substrate.

The above description of the present disclosure is provided for the purpose of illustration, and it would be understood by those skilled in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A Group 4 metal element-containing compound, represented by the following Chemical Formula 1:

[Chemical Formula 1]

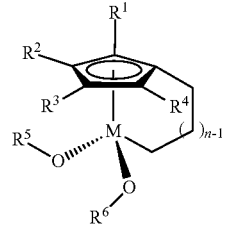

in the above Chemical Formula 1,

M is Ti, Zr or Hf, each of $R^1$ to $R^4$ is independently hydrogen or a linear or branched alkyl group having 1 to 4 carbon atoms, each of $R^5$ and $R^6$ is independently a linear or branched alkyl group having 1 to 4 carbon atoms, and n is an integer of from 1 to 3.

2. The Group 4 metal element-containing compound of claim 1, wherein M is Ti, Zr or Hf, each of $R^5$ and $R^6$ is independently $CH_3$, $C_2H_5$ or $CH(CH_3)_2$, and n is an integer of from 1 to 3.

3. The Group 4 metal element-containing compound of claim 2, wherein M is Ti, Zr or Hf, $R^5$ and $R^6$ are $CH_3$, and n is 2.

4. A method of preparing a Group 4 metal element-containing compound represented by the following Chemical Formula 1, comprising reacting a compound represented by the following Chemical Formula 2 with a linear or branched alcohol as $R^5OH$ and/or $R^6OH$ having 1 to 4 carbon atoms:

[Chemical Formula 2]

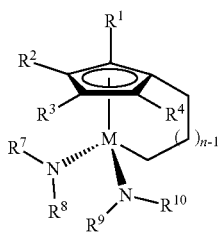

in the above Chemical Formula 2,
M is Ti, Zr or Hf,
each of $R^1$ to $R^4$ is independently hydrogen or a linear or branched alkyl group having 1 to 4 carbon atoms,
each of $R^7$ to $R^{10}$ is independently a linear or branched alkyl group having 1 to 4 carbon atoms, and
n is an integer of from 1 to 3;

[Chemical Formula 1]

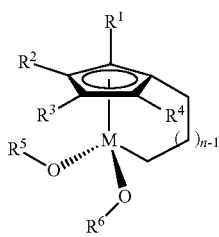

in the above Chemical Formula 1,
M is Ti, Zr or Hf,
each of $R^1$ to $R^4$ is independently hydrogen or a linear or branched alkyl group having 1 to 4 carbon atoms,
each of $R^5$ and $R^6$ is independently a linear or branched alkyl group having 1 to 4 carbon atoms, and
n is an integer of from 1 to 3.

5. A method of preparing a Group 4 metal element-containing compound represented by the following Chemical Formula 1, comprising reacting a compound represented by the following Chemical Formula 3 with M'OR$^5$ and/or M'OR$^6$ as a salt of an alkali metal M' of a linear or branched alcohol having 1 to 4 carbon atoms:

[Chemical Formula 3]

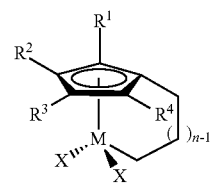

in the above Chemical Formula 3,
M is Ti, Zr or Hf,
each of $R^1$ to $R^4$ is independently hydrogen or a linear or branched alkyl group having 1 to 4 carbon atoms,
X is a halogen, and
n is an integer of from 1 to 3;

[Chemical Formula 1]

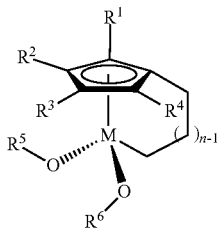

in the above Chemical Formula 1,
M is Ti, Zr or Hf,
each of $R^1$ to $R^4$ is independently hydrogen or a linear or branched alkyl group having 1 to 4 carbon atoms,
each of $R^5$ and $R^6$ is independently a linear or branched alkyl group having 1 to 4 carbon atoms, and
n is an integer of from 1 to 3.

6. A precursor composition for depositing a film, comprising a Group 4 metal element-containing compound of claim 1.

7. A method of depositing a Group 4 metal element-containing film, comprising forming a Group 4 metal element-containing film using a precursor composition for film depositing a film of claim 6.

* * * * *